(12) United States Patent
Unverdorben

(10) Patent No.: US 8,475,411 B2
(45) Date of Patent: Jul. 2, 2013

(54) SYSTEMS, KITS, AND METHODS FOR INFUSING FLUIDS TO A PATIENT

(75) Inventor: Martin Unverdorben, Pottstown, PA (US)

(73) Assignee: B. Braun Medical, Inc., Allentown, PA (US)

( * ) Notice: Subject to any disclaimer, the term of this patent is extended or adjusted under 35 U.S.C. 154(b) by 0 days.

(21) Appl. No.: 13/293,355

(22) Filed: Nov. 10, 2011

(65) Prior Publication Data

US 2013/0123702 A1    May 16, 2013

(51) Int. Cl.
*A61M 31/00*     (2006.01)

(52) U.S. Cl.
USPC ............................ 604/151; 604/131; 434/262

(58) Field of Classification Search
USPC ................................... 604/151, 131; 434/262
See application file for complete search history.

(56) References Cited

U.S. PATENT DOCUMENTS 7,753,883 B2 *    7/2010    Fournie et al. ................ 604/131

* cited by examiner

*Primary Examiner* — Laura Bouchelle
(74) *Attorney, Agent, or Firm* — RatnerPrestia

(57) ABSTRACT

Systems, kits, and methods for programming infusion systems are disclosed. A system comprises an infusion device and a mock pump set. The infusion device is programmable with at least one infusion protocol. The infusion device includes a pathway adapted to receive a pump set and at least one pump adapted to pump fluid through the pump set when the pump set is received in the pathway. The mock pump set is sized to be received in the pathway of the infusion device, and is not configured to receive fluid from the fluid container. A kit comprises the mock pump set. A method comprises inserting a mock pump set in a pathway of an infusion device and programming the infusion device with at least one infusion protocol while the mock pump set is received in the pathway.

18 Claims, 2 Drawing Sheets

SYSTEMS, KITS, AND METHODS FOR INFUSING FLUIDS TO A PATIENT

FIELD OF THE INVENTION

The present invention relates generally to infusion systems and, more particularly, to systems, kits, and methods for programming infusion systems.

BACKGROUND OF THE INVENTION

During medical treatment, it is often necessary to infuse fluids, such as medication or nutrients, into a patient's circulatory system. Conventionally, infusions are performed using infusion devices, which may include one or more pumps to infuse fluid to the patient at a predetermined rate and time. These infusion devices may be programmed according to predetermined infusion protocols, which are based, for example, on the fluid to be infused or the particular patient.

For safety purposes in a medical treatment setting, conventional infusion devices may restrict the personnel that are able to program the infusion device and initiate treatment. Further, conventional infusion devices may prevent medical personnel from programming the infusion device until a certain number of safety checks have been performed. However, measures taken to effect the above safety protocols may become burdensome in emergency situations, when the speed of medical treatment is of the essence. Accordingly, novel systems and methods for infusion in these situations are desired.

SUMMARY OF THE INVENTION

Aspects of the present invention relate to systems, kits, and methods for programming infusion systems.

In accordance with one aspect of the present invention, a system for infusing a fluid to a patient is disclosed. The system comprises an infusion device and a mock pump set. The infusion device is programmable with at least one infusion protocol for infusing the fluid to the patient. The infusion device includes a pathway adapted to receive a pump set configured to receive fluid from a fluid container and at least one pump adapted to pump fluid through the pump set when the pump set is received in the pathway. The mock pump set is sized to be received in the pathway of the infusion device. The mock pump set is not configured to receive fluid from the fluid container. The infusion device is configured to (i) prevent programming of the infusion device with the at least one infusion protocol when neither the pump set nor the mock pump set is received in the pathway and (ii) enable programming of the infusion device with the at least one infusion protocol when the mock pump set is received in the pathway.

In accordance with another aspect of the present invention, a kit for programming an infusion system to infuse a fluid to a patient is disclosed. The kit comprises a mock pump set sized to be received in a pathway of an infusion device. The mock pump set is not configured to receive fluid from a fluid container.

In accordance with yet another aspect of the present invention, a method for programming an infusion system to infuse a fluid to a patient is disclosed. The method comprises inserting a mock pump set in a pathway of an infusion device. The mock pump set is not configured to receive fluid from a fluid container. The method further comprises programming the infusion device with at least one infusion protocol while the mock pump set is received in the pathway.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The exemplary systems, kits, and methods disclosed herein are directed toward infusing a fluid to a patient. These embodiments are particularly suitable for use with infusion devices (such as infusion pumps) that include protocols for restricting programming of the infusion device. While the exemplary embodiments disclosed herein are described with reference to emergency medical treatment, it will be understood that their application and use is not so limited.

As an example, an infusion pump may include a safety check that prevents programming of the infusion device unless (i) the fluid in the fluid container is approved for infusion, and (ii) the pump set (including the tubing connected to the approved fluid container) is installed in the infusion pump. However, the infusion device may need to be used in an emergency setting, such as an emergency room or an operating room. In this case, it may be desirable to pre-program the infusion pump with the infusion protocol prior to the procedure, because there may not be time to pre-approve the fluid and install the pump set in the infusion pump during the procedure.

In such situations, the exemplary embodiments disclosed herein are particularly suitable for pre-programming the infusion device prior to actual installation of the pump set connected to the fluid container. The disclosed embodiments desirably ease the burden of programming infusion devices during emergency situations, without disabling the safety check software of those devices, which may still be desirable during normal operation.

Figure 1:
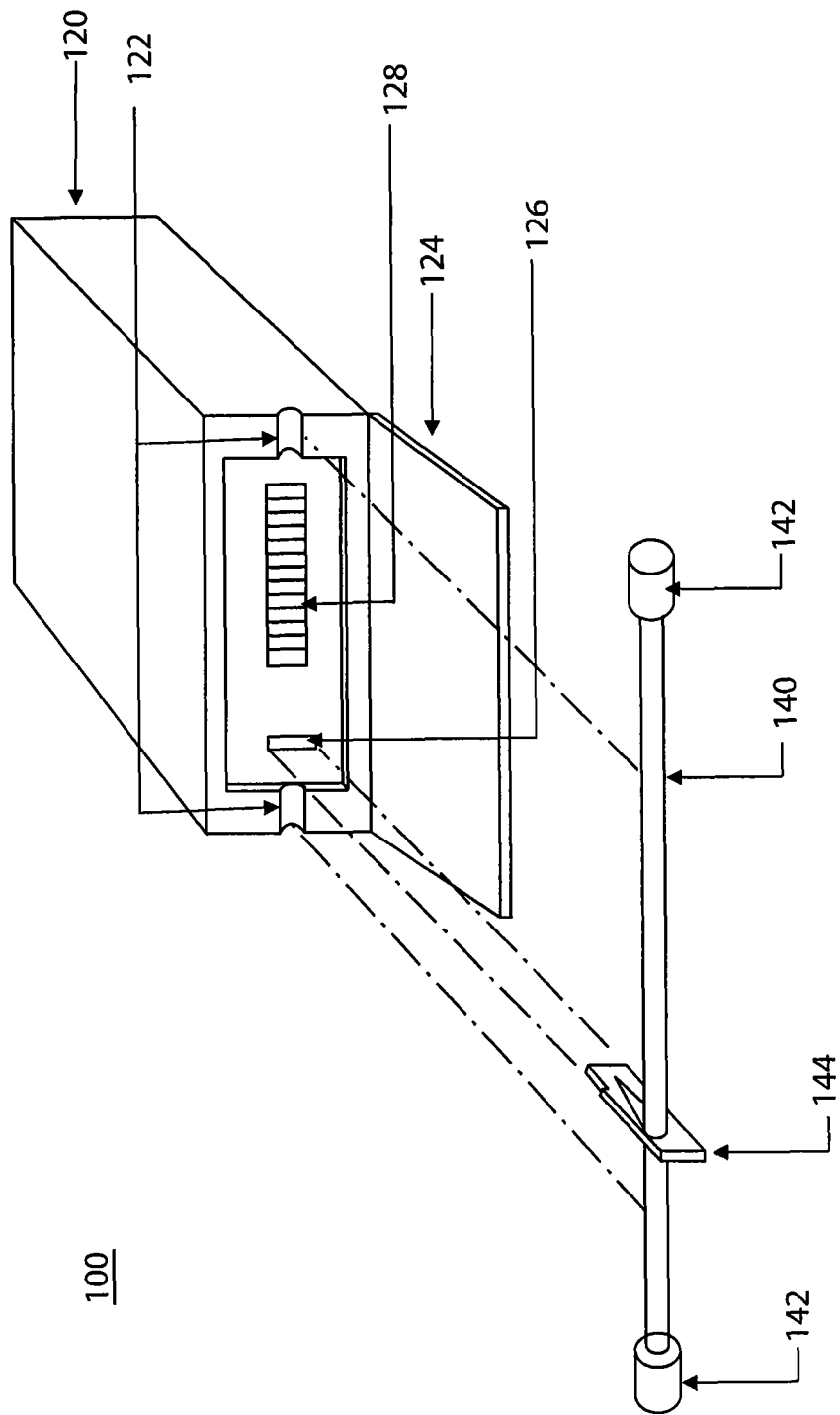
FIG. 1 is a diagram illustrating an exemplary system for infusing a fluid to a patient in accordance with aspects of the present invention.

Referring now to the drawings, FIG. 1 illustrates a system 100 for infusing fluid to a patient in accordance with aspects of the present invention. As a general overview, infusion system 100 includes an infusion device 120 and a mock pump set 140. Additional details of infusion system 100 are described herein.

Infusion device 120 infuses fluid to the patient. Infusion device 120 includes a pathway 122 and at least one pump 128.

Pathway 122 is adapted to receive a pump set. The pump set includes tubing configured to receive fluid from a fluid container (not shown). As used herein, the term "pathway" refers to any structure (such as a slot, retainer, or groove) adapted to receive and/or retain the tubing of the pump set. Pathway 122 may include a guide adapted to secure the tubing of the pump set in a desired location and orientation within infusion device 120. In an exemplary embodiment, infusion device 120 includes a door 124 adapted to secure the pump set within pathway 122 when closed. Infusion device 120 may also include a recess 126 adapted to receive an attachment (such as a clamp) of the pump set. Recess 126 may be usable to properly key the pump set within pathway 122 (i.e. ensure that the pump set is facing a proper direction).

Pump 128 is adapted to pump fluid through the pump set when the pump set is received in pathway 122. In an exemplary embodiment, pump 128 is a peristaltic pump. Suitable peristaltic pumps for use as pump 128 will be known to one of ordinary skill in the art from the description herein.

Infusion device 120 is programmable with at least one infusion protocol for infusing the fluid to the patient. In an exemplary embodiment, infusion device 120 includes a processor and an input device. The processor controls the programming of infusion device 120 with the at least one infusion protocol, and coordinates the operation of pump 128 in accordance with the at least one infusion protocol. The input device enables the receipt of information (e.g., the selected infusion protocol) from the user of infusion system 100. As will be explained in greater detail below, the processor may be configured to prevent programming of infusion device 120 with the selected infusion protocol when a pump set is not received in pathway 122, and to enable programming of infusion device 120 with the selected infusion protocol when a pump set is received in pathway 122. Where infusion device 120 includes recess 126, the processor may be configured to prevent programming of infusion device 120 when an attachment of the pump set is not received in recess 126 and door 124 has not been closed.

It will be understood that infusion device 120 is not limited to the above components, but may include alternative components and additional components, as would be understood by one of ordinary skill in the art from the description herein. In one particularly preferred embodiment, infusion device 120 may be the INFUSOMAT® SPACE infusion pump, provided by B. Braun Medical Inc., of Bethlehem, Pa.

Mock pump set 140 is sized to be received in pathway 122 of infusion device 120. As will be clear from the description herein, and from FIG. 1, mock pump set 140 differs from the pump set intended for use during normal operation of infusion device 120. This is because mock pump set 140 is not configured to receive fluid from the fluid container, or to deliver fluid to the patient. To the contrary, mock pump set 140 merely corresponds (or substantially corresponds) to the size (e.g. diameter) of the pump set that is intended to be positioned within pathway 122.

In an exemplary embodiment, mock pump set 140 is incapable of connection to the fluid container or to the patient. Mock pump set 140 may be closed at one or both ends of mock pump set 140, in order to prevent connection or prevent the receipt of fluid. For example, mock pump set 140 may include one or more fittings 142 received in the ends of tubing of the mock pump set 140, as shown in FIG. 1, in order to close the ends and prevent connection. Alternatively, mock pump set 140 may comprise a solid flexible member (as opposed to a tubular member) that corresponds (or substantially corresponds) to the size of the intended pump set.

It may be desirable to visually distinguish mock pump set 140 from the pump set that is intended to be used with infusion device 120, in order to prevent confusion during use of infusion device 120. For one example, fittings 142 may be shaped or sized so as to be easily identified by a user of mock pump set 140. Further, fittings 142 may have a color different from mock pump set 140 (e.g., bright or neon colors), in order to enable a user of infusion system 100 to easily visually identify fittings 142.

For another example, mock pump set 140 may be substantially shorter than the pump set that is intended to be used with infusion device 120. As shown in FIG. 1, mock pump set 140 may be substantially the same length as pathway 122 in infusion device 120, so as to minimize the portions of mock pump set 140 that protrude from infusion device 120. This may further assist the user in differentiating mock pump set 140 from the pump set that is intended to be used with infusion device 120.

For yet another example, mock pump set 140 may include a printed label indicating that it is to be used for programming only, and not for infusion. The label may desirably include patient or medication information, and/or one or more bar codes for identifying the patient or medication information, and/or the infusion protocol to be programmed into infusion device 120.

For still another example, the tubing of mock pump set 140 may be formed from or modified to include a material having a different color than the color of the tubing for the pump set intended to be used with infusion device 120. This different colored tubing may be visually identified by a user. Alternatively, infusion device 120 may include one or more sensors for detecting the color of the pump set inserted in pathway 122. In this embodiment, infusion device 120 may be configured to enable programming of infusion device 120 when a pump set having the color of mock pump set 140 is inserted in pathway 122. Still further, infusion device 120 may be configured to prevent activation of infusion device 120 unless a pump set having the color of the intended pump set is inserted in pathway 122. This may prevent inadvertent activation of infusion device 120 when mock pump set 140 is installed in pathway 122.

For yet another example, mock pump set 140 may include a particular fluid (e.g. a desired medication) for enabling programming of infusion device 120. The mock pump set 140 of this example may include a fill port for enabling insertion of fluid, and a vent to enable removal of air from the mock pump set 140 during fluid insertion, such that mock pump set 140 is still not configured to deliver the fluid to a patient. In this embodiment, infusion device 120 may include one or more sensors for detecting the fluid in the pump set inserted in pathway 122. Infusion device 120 may be configured to enable programming of infusion device 120 with a certain protocol only when a pump set having the correct fluid is inserted in pathway 122. This may prevent programming infusion device 120 with an incorrect protocol when mock pump set 140 is installed in pathway 122. The mock pump set 140 of this example is desirably disposable after use.

Mock pump set 140 may further include an attachment 144. In an exemplary embodiment, attachment 144 is a clamp, as shown in FIG. 1. The clamp may correspond to a clamp that would normally be used on the pump set that is intended to be used with infusion device 120. Attachment 144 may be usable to properly key mock pump set 140 within pathway 122 (i.e. to ensure that mock pump set 140 is facing a proper direction). Attachment 144 may be positioned on mock pump set 140 to mate with a correspond recess 126 of infusion device 120. This may be particularly important in situations in which the processor of infusion device 120 is configured to prevent programming of infusion device 120 with a selected infusion protocol when the attachment or clamp 144 is not received in recess 126.

The above described infusion system 100 may also form the basis of a kit for programming an infusion system to infuse a fluid to a patient in accordance with aspects of the present invention. The kit includes a mock pump set sized to be received in the pathway of an infusion device. The mock pump set is not configured to receive fluid from a fluid container, or to deliver fluid to a patient. To the contrary, the mock pump set merely corresponds (or substantially corresponds) to the size of the pump set that is intended to be used with the infusion device. The mock pump set of this kit may be usable with any of the above described embodiments of infusion device 120, and may comprise any of the features described above with respect to mock pump set 140.

Figure 2:
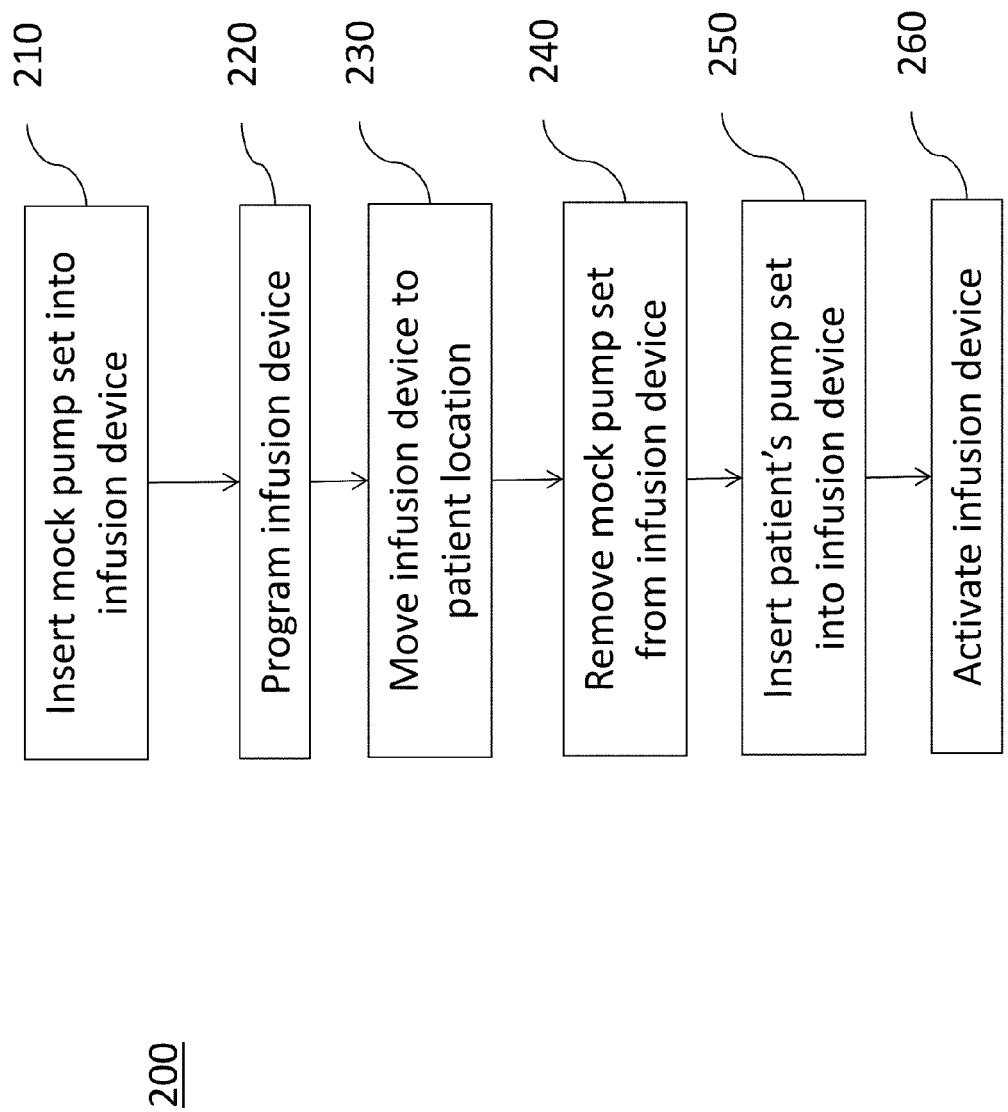
FIG. 2 is a flow chart illustrating an exemplary method for programming an infusion system to infuse a fluid to a patient in accordance with aspects of the present invention.

FIG. 2 shows an exemplary method 200 for programming an infusion system to infuse a fluid to a patient in accordance with aspects of the present invention. As a general overview, method 200 includes inserting a mock pump set into an infusion device, and programming the infusion device. Additional details of method 200 are described herein with respect to the components of infusion system 100.

In step 210, the mock pump set is inserted into the infusion device. In an exemplary embodiment, a user of infusion system 100 inserts mock pump set 140 into pathway 122 of infusion device 120. Mock pump set 140 is not configured to receive fluid from a fluid container, or to deliver fluid to a patient. Thus, the user does not connect mock pump set 140 to a fluid container, or to the patient. Where infusion device 120 includes recess 126, as set forth above, step 210 further includes inserting attachment 144 into recess 126 of infusion device 120.

As set forth above, the processor of infusion device 120 is configured to prevent programming of infusion device 120 with the selected infusion protocol when a pump set is not received in pathway 122 (i.e., neither an actual pump set nor a mock pump set). This software configuration may be desirable for infusion device 120 in order to provide a safety check that prevents programming of infusion device 120 unless (i) the fluid in the fluid container is approved for infusion, and (ii) the pump set (including the tubing connected to the approved fluid container) is installed in infusion device 120.

When mock pump set 140 is inserted into pathway 122, infusion device 120 (and its associated processor) cannot distinguish mock pump set 140 from the pump set that is intended to be used with the infusion device. This is because mock pump set 140 corresponds (or substantially corresponds) to the size of the pump set that is intended to be used with infusion device 120. Accordingly, the processor interprets mock pump set 140 as being the intended pump set (and as being connected to the correct fluid source), and enables programming of infusion device 120 with the selected infusion protocol.

In step 220, the infusion device is programmed. In an exemplary embodiment, the user of infusion system 100 programs infusion device 120 with the selected infusion protocol. The user must program infusion device 120 while mock pump set 140 is received in pathway 122 of infusion device 120, i.e., while the processor of infusion device 120 is enabling programming of infusion device 120.

In step 230, the infusion device is moved to the patient. In an exemplary embodiment, steps 210 and 220 are performed in a location remote from the patient, or before the patient has arrived in the location at which the patient will be connected for infusion. Accordingly, following programming of infusion device 120, infusion device 120 may be moved to the location of the patient, in order to prepare to treat the patient with infusion device 120.

In step 240, the mock pump set is removed from the infusion device. In an exemplary embodiment, mock pump set 140 is removed from pathway 122. Mock pump set 140 may be removed from pathway 122 when infusion device 120 is ready to be used (i.e., needed to perform an infusion). Infusion device 120 is configured to retain the programmed infusion protocol after removal of mock pump set 140. In one embodiment, the infusion device 120 may retain the programmed infusion protocol until the infusion device 120 is switched off. In other embodiments, the infusion device 120 may retain the programmed infusion protocol after the programmed infusion device is switched off and/or for a predetermined period of time.

In step 250, the patient's pump set is inserted into the infusion device. In an exemplary embodiment, the user of infusion system 100 inserts the pump set intended to be used with infusion device 120 into pathway 122. The intended pump set is coupled or configured to be coupled to a fluid container and is configured to provide fluid from the fluid container to the patient.

In step 260, the infusion device is activated. In an exemplary embodiment, infusion device 120 is activated to operate with the pre-programmed infusion protocol to infuse fluid to the patient using the intended pump set, without requiring the step of programming infusion device 120 after insertion of the intended pump set.

It will be understood that method 200 is not limited to the above steps, but may include alternative steps and additional steps, as would be understood by one of ordinary skill in the art from the description herein. For one example, steps 230-260 occur after programming of the infusion device is completed, and therefore, may be omitted.

With the above-described method, the use of infusion system 100, and particularly mock tube set 140, speeds up the process of preparing infusion device 120 for infusion by enabling pre-programming of infusion device 120 with the desired infusion protocol. This desirably eases the burden of programming infusion device 120 during emergency situations, without disabling the safety check software of infusion device 120, which may still be desirable during normal operation.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for infusing a fluid to a patient comprising:
an infusion device programmable with at least one infusion protocol for infusing the fluid to the patient, the infusion device including a pathway adapted to receive a pump set configured to receive fluid from a fluid container and at least one pump adapted to pump fluid through the pump set when the pump set is received in the pathway; and
a mock pump set sized to be received in the pathway of the infusion device, the mock pump set not configured to receive fluid from the fluid container;
wherein the infusion device is configured to (i) prevent programming of the infusion device with the at least one infusion protocol when neither the pump set nor the mock pump set is received in the pathway and (ii) enable programming of the infusion device with the at least one infusion protocol when the mock pump set is received in the pathway, and
wherein the mock pump set has substantially the same length as the pathway of the infusion device.

2. The system of claim 1, wherein the mock pump set is incapable of connection to the fluid container or the patient.

3. The system of claim 1, wherein
the mock pump set comprises an attachment attached to the mock pump set;
the infusion device further comprises a recess adapted to receive the attachment; and wherein the infusion device is configured to prevent programming unless the attachment is received in the recess.

4. The system of claim 2, wherein the mock pump set is closed on at least one end.

5. The system of claim 4, wherein the closed end comprises a fitting received in the mock pump set.

6. The system of claim 5, wherein the fitting has a color different from the mock pump set in order to enable a user to easily visually identify the fitting.

7. A kit for programming an infusion system to infuse a fluid to a patient, the infusion system comprising an infusion device programmable with at least one infusion protocol for infusing the fluid to the patient, the infusion device including a pathway adapted to receive a pump set configured to receive fluid from a fluid container and at least one pump adapted to pump fluid through the pump set when the pump set is received in the pathway; the kit comprising:
  a mock pump set sized to be received in the pathway of the infusion device, the mock pump set not configured to receive fluid from the fluid container,
  wherein the mock pump set has substantially the same length as the pathway of the infusion device.

8. The kit of claim 7, wherein the mock pump set is incapable of connection to the fluid connector or the patient.

9. The kit of claim 7, wherein the infusion device comprises a recess adapted to receive an attachment; and
  the mock pump set comprises the attachment attached to the mock pump set.

10. The kit of claim 8, wherein the mock pump set is closed on at least one end.

11. The kit of claim 10, wherein the closed end comprises a fitting received in the mock pump set.

12. The kit of claim 11, wherein the fitting has a color different from the mock pump set in order to enable a user to easily visually identify the fitting.

13. A system for infusing a fluid to a patient comprising:
  an infusion device programmable with at least one infusion protocol for infusing the fluid to the patient, the infusion device including a pathway adapted to receive a pump set configured to receive fluid from a fluid container and at least one pump adapted to pump fluid through the pump set when the pump set is received in the pathway; and
  a mock pump set sized to be received in the pathway of the infusion device, the mock pump set not configured to receive fluid from the fluid container;
  wherein the infusion device is configured to (i) prevent programming of the infusion device with the at least one infusion protocol when neither the pump set nor the mock pump set is received in the pathway and (ii) enable programming of the infusion device with the at least one infusion protocol when the mock pump set is received in the pathway,
  wherein the mock pump set is incapable of connection to the fluid container or the patient,
  wherein the mock pump set is closed on at least one end, and
  wherein the closed end comprises a fitting received in the mock pump set.

14. The system of claim 13, wherein the fitting has a color different from the mock pump set in order to enable a user to easily visually identify the fitting.

15. The system of claim 13, wherein
  the mock pump set comprises an attachment attached to the mock pump set;
  the infusion device further comprises a recess adapted to receive the attachment; and
  wherein the infusion device is configured to prevent programming unless the attachment is received in the recess.

16. A kit for programming an infusion system to infuse a fluid to a patient, the infusion system comprising an infusion device programmable with at least one infusion protocol for infusing the fluid to the patient, the infusion device including a pathway adapted to receive a pump set configured to receive fluid from a fluid container and at least one pump adapted to pump fluid through the pump set when the pump set is received in the pathway; the kit comprising:
  a mock pump set sized to be received in the pathway of the infusion device, the mock pump set not configured to receive fluid from the fluid container,
  wherein the mock pump set is incapable of connection to the fluid connector or the patient,
  wherein the mock pump set is closed on at least one end, and
  wherein the closed end comprises a fitting received in the mock pump set.

17. The kit of claim 16, wherein the fitting has a color different from the mock pump set in order to enable a user to easily visually identify the fitting.

18. The kit of claim 16, wherein the infusion device comprises a recess adapted to receive an attachment; and
  the mock pump set comprises the attachment attached to the mock pump set.

* * * * *